United States Patent
Aparicio et al.

(10) Patent No.: US 7,381,288 B2
(45) Date of Patent: Jun. 3, 2008

(54) SPECIMEN LABELING SYSTEM

(75) Inventors: Karina M. Aparicio, Los Angeles, CA (US); Brian Mach, Thousand Oaks, CA (US); Brenda Dawes, New Port Richey, FL (US); Wendell Franke, Monson, MA (US); Lucy Reday, Winnetka, CA (US)

(73) Assignee: Sandel Medical Industries LLC, Chatsworth, CA (US)

( * ) Notice: Subject to any disclaimer, the term of this patent is extended or adjusted under 35 U.S.C. 154(b) by 179 days.

(21) Appl. No.: 11/266,938

(22) Filed: Nov. 4, 2005

(65) Prior Publication Data

US 2006/0100541 A1 May 11, 2006

Related U.S. Application Data

(60) Provisional application No. 60/625,815, filed on Nov. 8, 2004.

(51) Int. Cl.
*B32B 37/12* (2006.01)
*B32B 38/14* (2006.01)
*B65C 1/10* (2006.01)
*B65C 3/08* (2006.01)
*A61F 10/00* (2006.01)

(52) U.S. Cl. ........... 156/277; 156/DIG. 1; 156/DIG. 9; 600/562; 422/99; 422/102

(58) Field of Classification Search ............. 156/277, 156/DIG. 1, DIG. 9; 600/562; 422/99, 422/102, 941, 944, 945
See application file for complete search history.

(56) References Cited

U.S. PATENT DOCUMENTS

| | | | | |
|---|---|---|---|---|
| 5,000,484 | A | * | 3/1991 | Phelan et al. ............. 283/75 |
| 5,383,472 | A | * | 1/1995 | Devlin et al. ............. 600/584 |
| 5,554,151 | A | * | 9/1996 | Hinchliffe ................ 606/1 |
| 5,609,827 | A | * | 3/1997 | Russell et al. ............ 422/102 |
| 5,679,570 | A | * | 10/1997 | Heckenmuller et al. . 435/287.9 |
| 6,258,327 | B1 | * | 7/2001 | Tatum ..................... 422/102 |
| 7,172,558 | B2 | * | 2/2007 | Olson, Jr. ................ 600/562 |
| 2006/0191951 | A1 | * | 8/2006 | Mathews .................. 221/210 |
| 2007/0183938 | A1 | * | 8/2007 | Booker ..................... 422/102 |

* cited by examiner

*Primary Examiner*—Melvin Mayes
(74) *Attorney, Agent, or Firm*—Perkins Coie LLP; Kenneth H. Ohriner

(57) ABSTRACT

A method for handling, labeling, identifying and/or organizing specimens removed from a patient during surgery performed in the sterile field may include placing a specimen identification sheet in or near the sterile field. The specimen may be placed onto one section of the specimen identification sheet. The section advantageously has an identifier, such as a printed number or letter, or combinations of them. The section may then be marked with specimen identifying information. The section with the specimen may optionally be separated from the specimen identification sheet. The specimen is transferred from the section into or onto a container. The container can be marked with specimen identifying information, using a marker and a blank label, and/or with a pre-printed label.

7 Claims, 6 Drawing Sheets

FIG. 5

| Aortic Plaque | Hemorrhoids |
|---|---|
| Appendix | Hernia Sac L___R |
| Adenoids | Lesion L___R |
| Biopsy L___R | Liver Tissue |
| Bladder Tissue | Lung Tissue |
| Bowel Segment | Lymph Node |
| Breast Tissue L___R | Nasal Polyp |
| Brushings | Ovary L___R |
| Carotid Plaque L___R | Parathyroid Tissue |
| Clot, AV Graft | Pilonidal Cyst |
| Disc Tissue | Placenta |
| Ethmoid Sinus | Skin Tag |
| Fallopian Tube L___R | Prostate Tissue |
| Femoral Head L___R | Suture Marker At ___ O'Clock |
| Femoral Plaque L___R | Suture Marker At ___ O'Clock |
| Foreign Body | Suture Marker At ___ O'Clock — 36 |
| Frozen Section L___R | Thyroid Tissue |
| Gallbladder | Turbinates — 38 |
| Ganglion Cyst | Uterus |
| Hardware L___R | Vas Deferens L___R |

SIDE VIEW:

SIDE VIEW:

SPECIMEN LABELING SYSTEM

PRIORITY CLAIM

This application claims priority to U.S. Provisional Patent Application Ser. No. 60/625,815, filed Nov. 8, 2004, and incorporated herein by reference.

FIELD OF THE INVENTION

The field of the invention is specimen collection during surgery. The invention further relates to subsequent handling of surgically removed specimens.

BACKGROUND OF THE INVENTION

Specimens are routinely collected during various surgical procedures. The specimens may be tissue samples taken from a surgical site, an internal organ, or other body part. The collected specimens are ordinarily then sent for testing. The test results can provide information helpful in the diagnosis, treatment, and recovery of the patient. Typically, specimens have been collected in medicine cups or other similar containers. Alternatively, specimens have simply been placed onto surgical drapes or towels in, or adjacent to, the sterile field. There is currently no standard technique for specimen collection, labeling, or handling. Accordingly, these important aspects of surgical practice vary widely.

The current use of medicine cups, drapes, towels, etc. for collection of surgical specimens can make identification of the specimen very difficult. It is important that the specimen be identified with information describing the location in the body from where the specimen was taken. Especially during procedures where larger numbers of specimens are involved, reliably identifying each specimen can require considerable effort by the surgical team, especially the surgical nurse.

Accordingly, improved specimen handling and labeling systems and methods are needed.

SUMMARY OF THE INVENTION

A method for handling, labeling, identifying and/or organizing specimens removed from a patient during surgery performed in the sterile field may include placing a specimen identification sheet in or near the sterile field. The specimen may be placed onto one section of the specimen identification sheet. The section advantageously has an identifier, such as a printed number or letter, or combinations of them. The section may then be marked with specimen identifying information. The section with the specimen may optionally be separated from the specimen identification sheet. The specimen is transferred from the section into or onto a container. The container can be marked with specimen identifying information, using a marker and blank label, or with a pre-printed label.

Other features and advantages will be shown and described. The invention resides as well in the systems, kits, components and methods described.

BRIEF DESCRIPTION OF THE DRAWINGS

FIG. 5 is a top view of preprinted labels.

DETAILED DESCRIPTION

Figure 1:
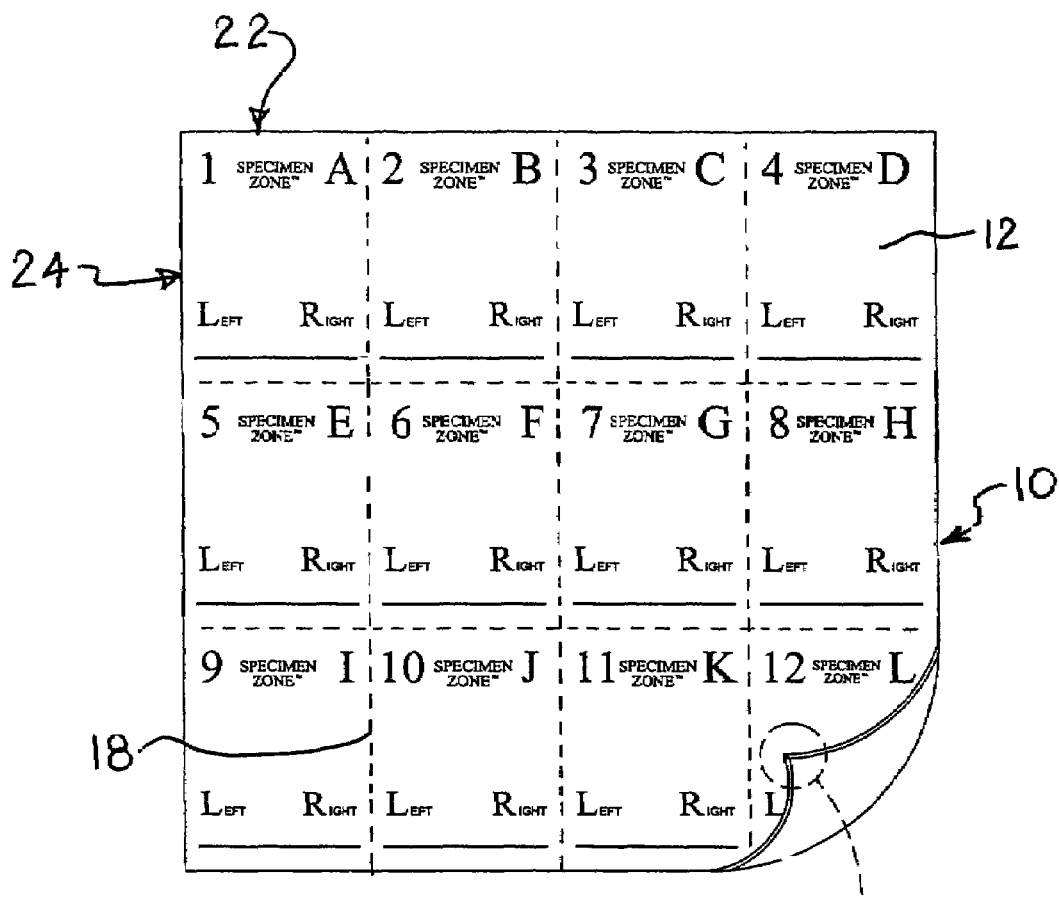
FIG. 1 is a top perspective view of a preprinted specimen sheet.
Figure 2:
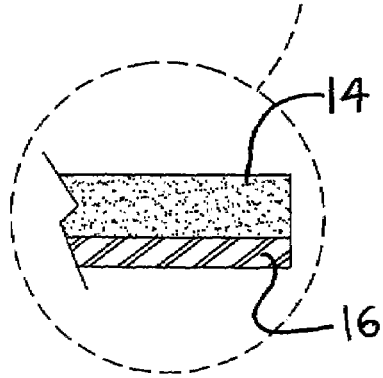
FIG. 2 is a partial section view of the sheet shown in FIG. 1.

Systems for identification, labeling, organizing and transferring of specimens are described. Turning now in detail to the drawings, as shown in FIGS. 1 and 2, a specimen collection sheet 10 may be divided into multiple sections 12 by perforations 18. Although the sheet 10 may also be provided as a single layer of material, a two-layer design is shown in FIG. 2. The top layer 14 is advantageously a non-woven and non-absorbent material. The bottom layer 16, if any, may be a different material, such as polyolefin. The sheet materials are advantageously resistant to formalin and similar chemical solutions. The sheet 10 is advantageously divided into multiple square or rectangular sections 12 by the perforations 18. The sheet may or may not have an adhesive backing. The perforations 18 are advantageously provided in a way that no foreign particles debris are released. Other section dividing techniques, such as fold lines, score lines, grooves, thinned sections, etc. may also be used.

The specimen sheet 10 shown in FIG. 1 has four columns 22 and three rows 24, providing a total of 12 sections. The sheet 10 may of course also be provided in other configurations having greater or fewer columns or rows. Single row sheets having 1, 2, 3, 4, or more sections may also be used. In place of an integral or one piece sheet 10, individual pieces or sections 12 may also be used. For example, separate sections 12 may be placed in a designated area, with specimens then placed onto the individual sections. The sections may be square, round, triangular, rectangular, or have some other shape.

The specimen sheet 10, or the top layer 14 (if used) is advantageously provided with a color which contrasts with commonly used surgical sheets and towels and which also contrasts with the generally red color of the specimens to be collected. Such contrasting colors may include, but are not limited to, green, yellow, white, etc.

Although FIG. 1 shows all of the sections 12 as having the same dimensions and size, in alternative designs, sections of varying size may be used. In addition, although square or rectangular sections 12 are shown, sections having other shapes may also be used. A strip or single row of sections may be provided in a kit along with other components, as described e.g., in U.S. Pat. No. 6,955,002, incorporated herein by reference. The sections 12 may alternatively have various forms, such as the flat sheet material shown in FIGS. 1 and 2. Alternatively, the sections 12 may equivalently be provided in the form of pre-separated sections, or individual dishes, containers, or other pieces. Alternatively, combinations of various types of pieces, such as the sections 12 shown in FIG. 1, the cups 64 shown in FIG. 10, or other containers or carriers, may be used in combination.

Figure 3:
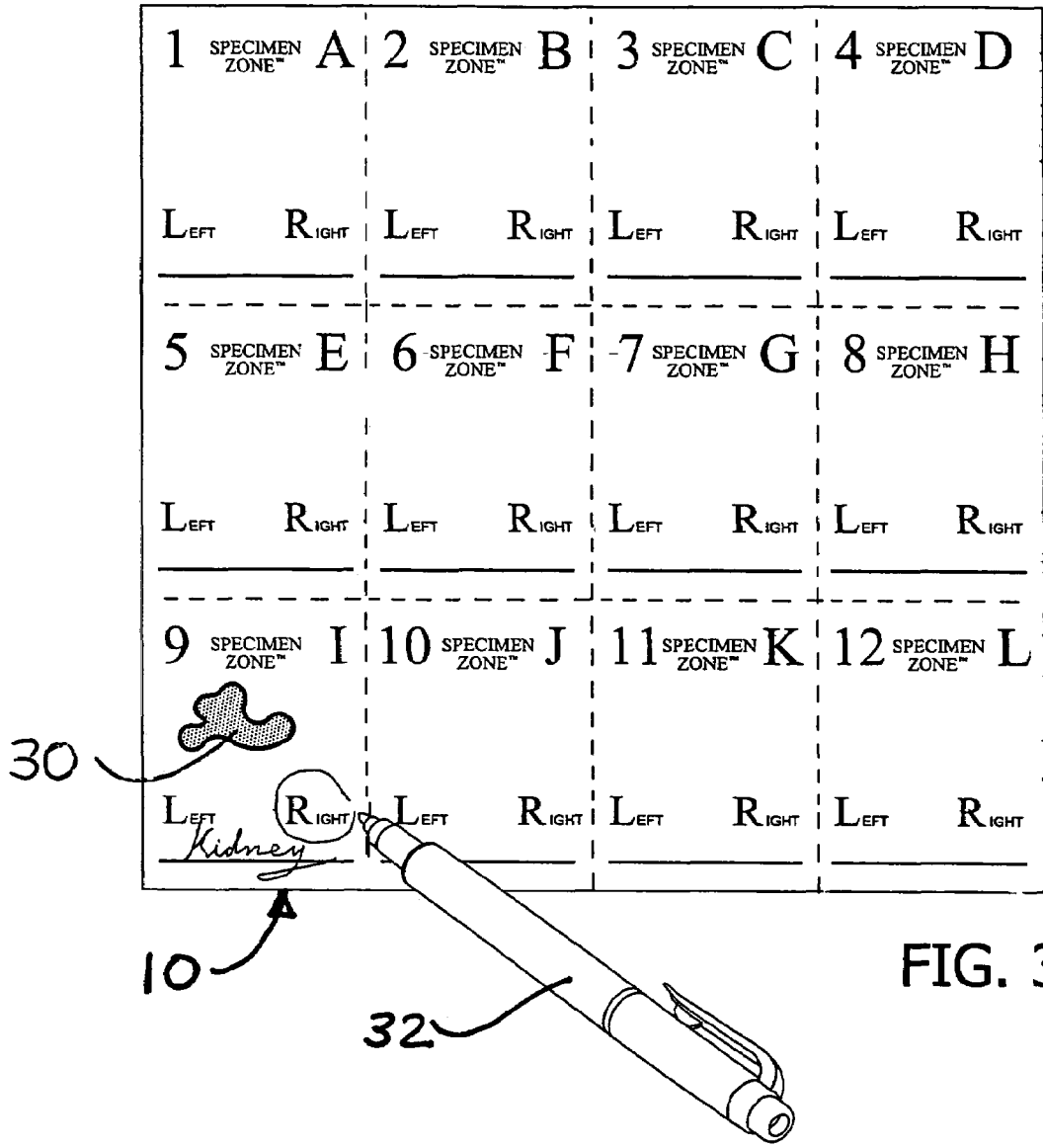
FIG. 3 shows the specimen sheet of FIG. 1 in use.
Figure 4:
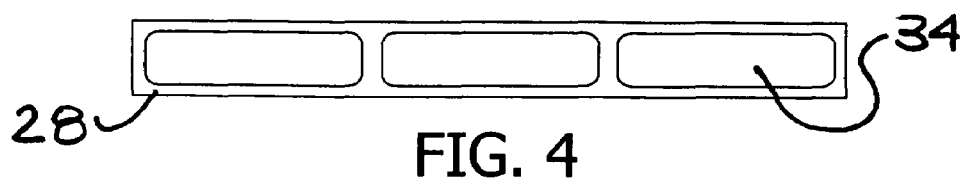
FIG. 4 is a top view of blank labels.

As shown in FIGS. 1 and 3, advantageously each of the sections 12 on the specimen sheet 10 is labeled with a number (e.g., 1-12), or a letter (e.g., A-L), or both. In addition, each of the sections 12 may also be marked with the captions "left" and "right," or simply "L" and "R." The markings may be printed onto the specimen sheet 10.

Turning now to FIGS. 3-8, in use, the specimen sheet 10 is placed in the sterile field. If the sheet 10 is provided with an adhesive back, the sheet may be adhered to a surgical sheet or other surface. A specimen removed from the patient is placed onto one of the sections 12. A member of the surgical team, typically a nurse, may then use a marker 32 to identify the specimen 30. For example, in FIG. 3, the specimen is identified by writing "kidney" on the section 12 onto which the specimen 30 was placed. A left or right designation may also be made, to further identify where the specimen was taken from. The marker generally will have permanent ink, although other types of markers may be used.

Figure 6:
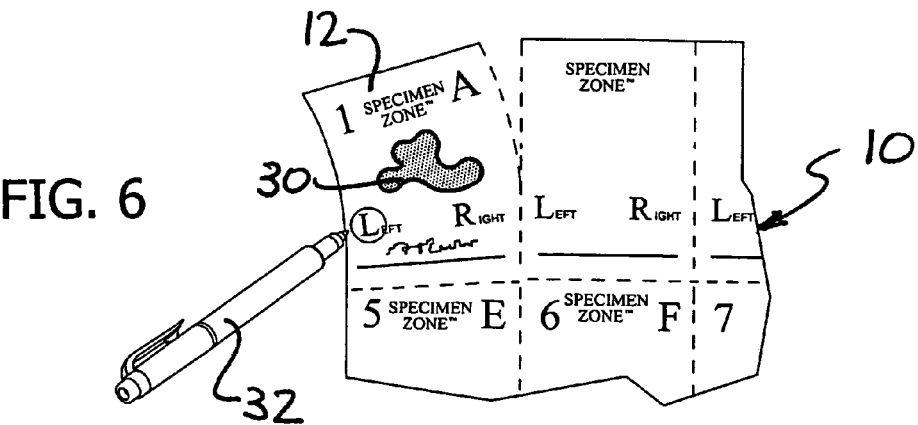
FIGS. 6, 7, and 8 are perspective views showing a sequence of steps for use of the specimen sheet and labels shown in FIGS. 1-5.
Figure 7:
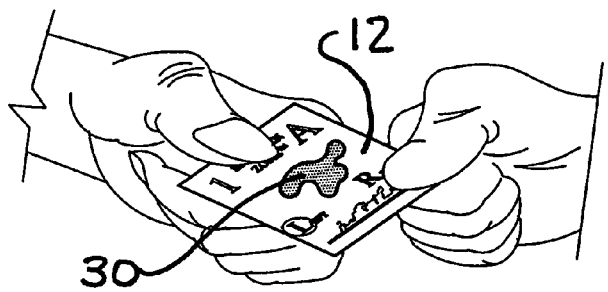
Figure 8:
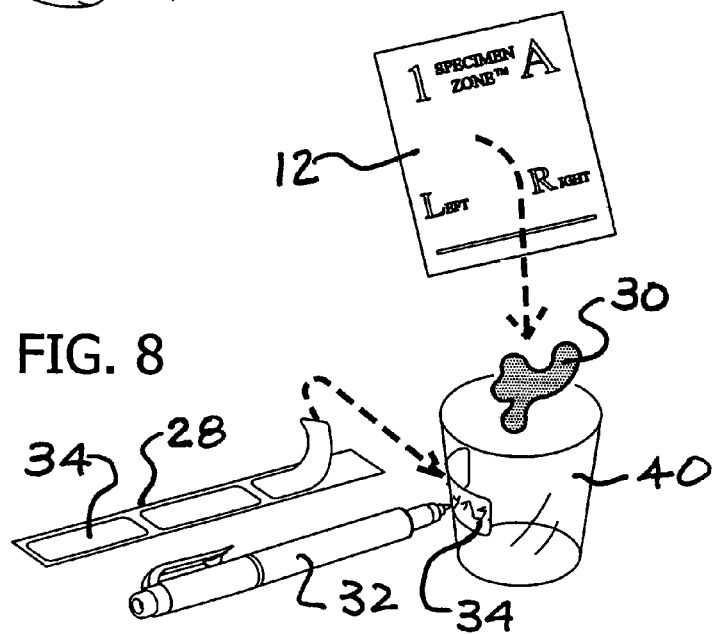

Referring to FIGS. 6-8, the section 12 holding the specimen 30 may then be separated from the sheet 10, typically by tearing along the perforations 18. Referring to FIG. 7, the nurse working within the sterile field (shown as the gloved hand on the right side of FIG. 7) passes the section 12 carrying the specimen 30 to a circulating nurse (or other personnel). As shown in FIG. 8, the circulating nurse then removes the specimen 30 from the section 12. The specimen 30 may be placed into a surgical cup 40 or other container, dish, or carrier. A blank label 34 having an adhesive back is removed from a label strip 28 and placed onto the cup or container 40. The description of the specimen 30 on the section 12 is then written onto the blank label 34. Alternatively, preprinted labels, as shown in FIG. 5, may also be used. In this case, the appropriate preprinted label 38 is removed from the sheet 36 of preprinted labels, and is applied to the cup 40. A label may be used to mark the container, or the container may be marked (directly on the container) using a marker. The cup 40 may then be moved to another location for running tests on the specimen 30. The sheet 10, or separate sections 12, may be provided as a kit, along with one or more of the marker, labels, the cup 40, optionally with other components as well. The kit and its components may be provided in a sterile condition.

Figure 9:
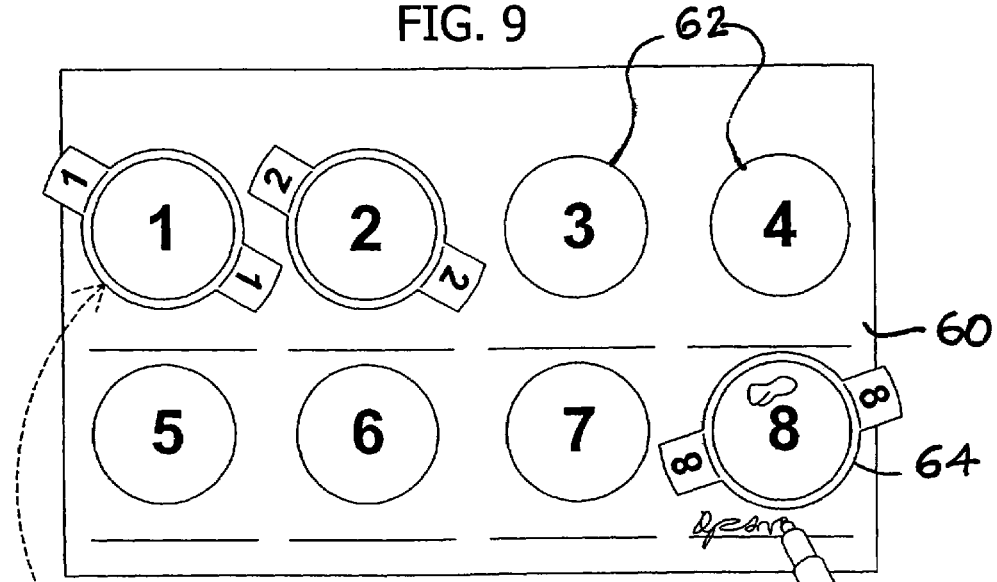
FIG. 9 is a top view of an alternative specimen collection system.
Figure 10:
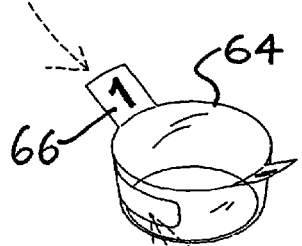
FIG. 10 is a perspective view of a specimen cup used in the system shown in FIG. 9.
Figure 11:
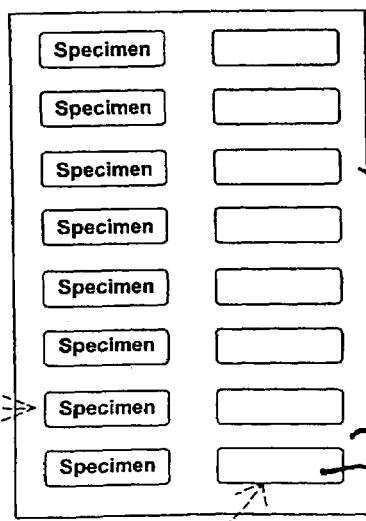
FIG. 11 is a top view of an alternative sheet of labels.

FIGS. 9-11 show an alternative embodiment including a sheet 60 having pre-printed areas or locations 62. In this design, the section 12 takes the form of cups or dishes 64 advantageously having tabs 66 marked with numbers. In use, the sheet 60 is laid out onto the sterile field or in another area. As one or more specimens are taken from the patient, they are placed into one of the cups 64 on the sheet 60. The cup 64 may be made of plastic or other material. Typically, the cup or dish 64 is circular, and approximately one inch tall. A blank label, or a preprinted label, is then applied to the cup 64, or onto the sheet 60 itself. The marker 32 can be used to write on a blank label, or directly onto a container.

The tabs 66 on the cups 64 can be used to transfer the cup from the sterile field to the non-sterile field. The tabs 64 may also be used to tip the cup 64, to transfer a specimen 30, without compromising sterility. The marker 32 may also be used to write directly onto the sheet 60.

Figure 12:
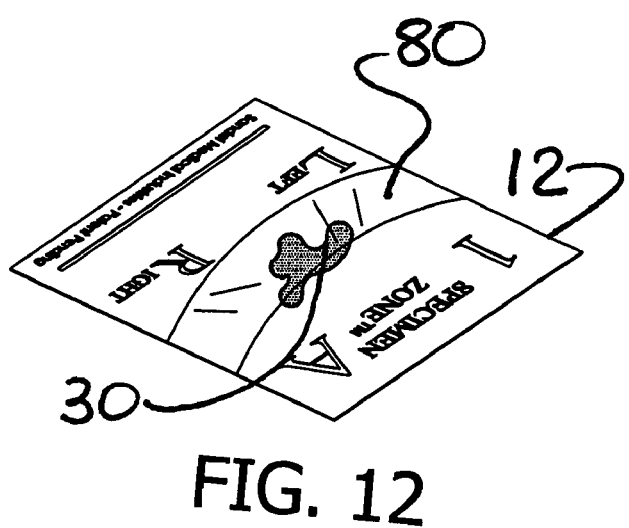
FIG. 12 is a perspective view of an alternative specimen collector.
Figure 13:
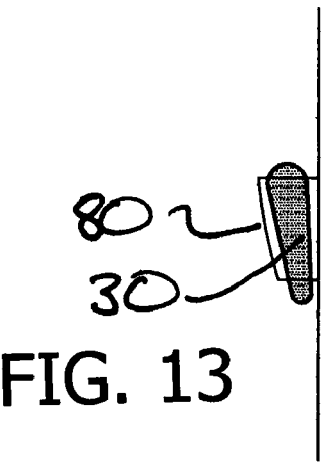
FIG. 13 is a side view of the specimen collector shown in FIG. 12.
Figure 14:
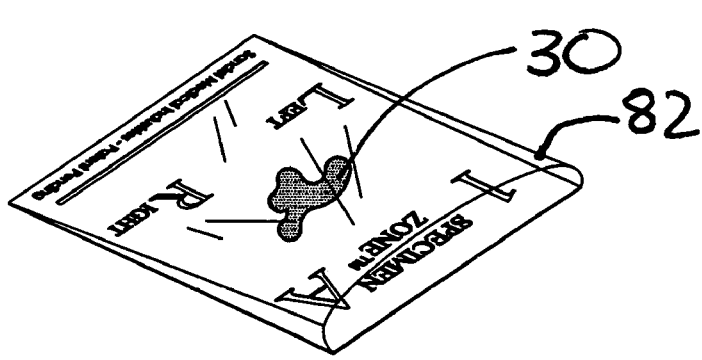
FIG. 14 is a perspective view of another alternative specimen collector.
Figure 15:
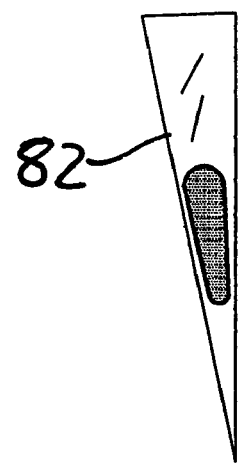
FIG. 15 is a side view of the specimen collector shown in FIG. 14.

FIGS. 12-15 show additional alternative designs having a sleeve 80 over each of the sections 12 of the sheet 10. This allows the user to tear the section 12 off of the sheet 10, slip the specimen 30 inside of the sleeve 80, and then transport the specimen. As shown in FIGS. 12 and 13, the sleeve 80 is in the form of a relatively narrow band overlying the specimen 30. A wider sheet with closed bottom, in the form of an envelope 82, as shown in FIGS. 14 and 15, may alternatively be used. The sleeve 80 or envelope 82 may be transparent.

In a more basic method of the invention, sections 12, cups 64, or other container or carriers are placed in or adjacent to the sterile field during surgery. These sections, cups, or carriers are identified by numbers, letters, or combinations of them (including words) via printing or labeling. Specimens are then placed into or onto the sections, cups, or containers. The sections, cups, or containers holding or carrying the specimens are then moved to another location.

Thus, novel systems, components, and methods have been shown and described. Various changes and modifications may of course be made without departing from the spirit and scope of the invention. The invention, therefore, should not be limited, except to the following claims and their equivalents.

The invention claimed is:

1. A method for handling, labeling, identifying and/or organizing specimens removed from a patient during surgery performed in the sterile field, comprising:
   placing a specimen identification sheet in or near the sterile field, with the specimen identification sheet having a plurality of sections, and with each section having at least one identifier;
   placing a specimen onto a section of the specimen identification sheet;
   marking the section with specimen identifying information;
   separating the section with the specimen from the specimen identification sheet;
   moving the section with the specimen away from the sterile field;
   transferring the specimen from the section into or onto a container; and
   marking the container with specimen identifying information.

2. The method of claim 1 wherein the section is marked with specimen identifying information by writing on the section.

3. The method of claim 1 wherein the section is marked with specimen identifying information by placing a label on the section.

4. The method of claim 1 wherein the section is separated from the specimen identification sheet by tearing the section away from the sheet along a perforation line.

5. The method of claim 1 wherein the container is marked with specimen identifying information by applying a label onto the container.

6. The method of claim 5 further comprising the step of writing specimen identifying information on the label.

7. The method of claim 1 wherein the container is marked with specimen identifying information by applying a preprinted label onto the container.

* * * * *